(12) United States Patent
Geiste et al.

(10) Patent No.: US 6,681,978 B2
(45) Date of Patent: Jan. 27, 2004

(54) SURGICAL STAPLER

(75) Inventors: Robert J. Geiste, Milford, CT (US); Mitchell J. Palmer, New Milford, CT (US); Lisa W. Heaton, Norwalk, CT (US); Robert C. Savage, Stratford, CT (US); Jon Wilson, Fairfield, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/765,805

(22) Filed: Jan. 19, 2001

(65) Prior Publication Data

US 2001/0002029 A1 May 31, 2001

Related U.S. Application Data

(60) Continuation of application No. 09/366,583, filed on Aug. 4, 1999, now Pat. No. 6,202,914, which is a division of application No. 08/549,580, filed on Oct. 27, 1995, now Pat. No. 5,941,442.

(51) Int. Cl.[7] .............................................. A61B 17/068
(52) U.S. Cl. ................... 227/176.1; 227/19; 227/180.1
(58) Field of Search ............................... 227/19, 175.1, 227/176.1, 180.1, 178.1

(56) References Cited

U.S. PATENT DOCUMENTS

| 3,079,606 A | 3/1963 | Bobrov et al. |
|---|---|---|
| 3,490,675 A | 1/1970 | Green et al. |
| 3,499,591 A | 3/1970 | Green |
| 4,064,881 A | 12/1977 | Meredith |
| 4,111,206 A | 9/1978 | Vishnevsky |
| 4,383,634 A | 5/1983 | Green |
| 4,391,401 A | 7/1983 | Moshofsky |
| 4,429,695 A | 2/1984 | Green |
| 4,520,817 A | 6/1985 | Green |
| 4,556,058 A | 12/1985 | Green |
| 4,592,498 A | 6/1986 | Braun et al. |
| 4,606,343 A | 8/1986 | Conte et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,664,305 A | 5/1987 | Blake, III et al. |
| 4,767,044 A | 8/1988 | Green |
| 4,821,942 A | 4/1989 | Richards et al. |
| 4,863,088 A | 9/1989 | Redmond et al. |
| 4,944,443 A | 7/1990 | Oddsen et al. |
| 4,955,959 A | 9/1990 | Tompkins et al. |
| 4,978,049 A | 12/1990 | Green |
| 5,031,814 A | 7/1991 | Tompkins et al. |
| 5,040,715 A | 8/1991 | Green et al. |
| 5,065,929 A | 11/1991 | Schulze et al. |
| 5,083,695 A | 1/1992 | Foslien et al. |
| 5,106,008 A | 4/1992 | Tompkins et al. |
| 5,141,144 A | 8/1992 | Foslien et al. |

(List continued on next page.)

FOREIGN PATENT DOCUMENTS

EP          8365153          8/1995

*Primary Examiner*—Scott A. Smith

(57) ABSTRACT

A surgical stapler is disclosed which includes a first body portion supporting an anvil plate defining a fastener forming surface, and a second body portion configured to releasably mate with the first body portion. A disposable loading unit is removably supported in the second body portion and includes a cartridge defining a plurality of slots, a plurality of surgical fasteners disposed in the slots, a plurality of ejectors positioned adjacent the surgical fasteners, and a wedged actuator configured to enter into and translate through the cartridge to sequentially interact with the ejectors. An elongated actuation member is mounted for longitudinal movement within the second body portion and is releasably engagable with the wedged actuator, whereby longitudinal movement of the actuation member causes the wedged actuator to interact with the ejectors, driving the surgical fasteners from the cartridge to be formed against the anvil plate.

20 Claims, 14 Drawing Sheets

U.S. PATENT DOCUMENTS

| | | |
|---|---|---|
| 5,156,614 A | 10/1992 | Green et al. |
| RE34,519 E | 1/1994 | Fox et al. |
| 5,326,013 A | 7/1994 | Green et al. |
| 5,352,238 A | 10/1994 | Green et al. |
| 5,366,133 A | 11/1994 | Geiste |
| 5,415,334 A | 5/1995 | Williamson, IV et al. |
| 5,415,335 A | 5/1995 | Knodell, Jr. |
| 5,445,304 A | 8/1995 | Plyley et al. |
| 5,447,265 A | 9/1995 | Vidal et al. |
| 5,470,006 A | 11/1995 | Rodak |
| 5,478,003 A | 12/1995 | Green et al. |
| 5,485,952 A | 1/1996 | Fontayne |
| 5,752,644 A | 5/1998 | Botanos et al. |

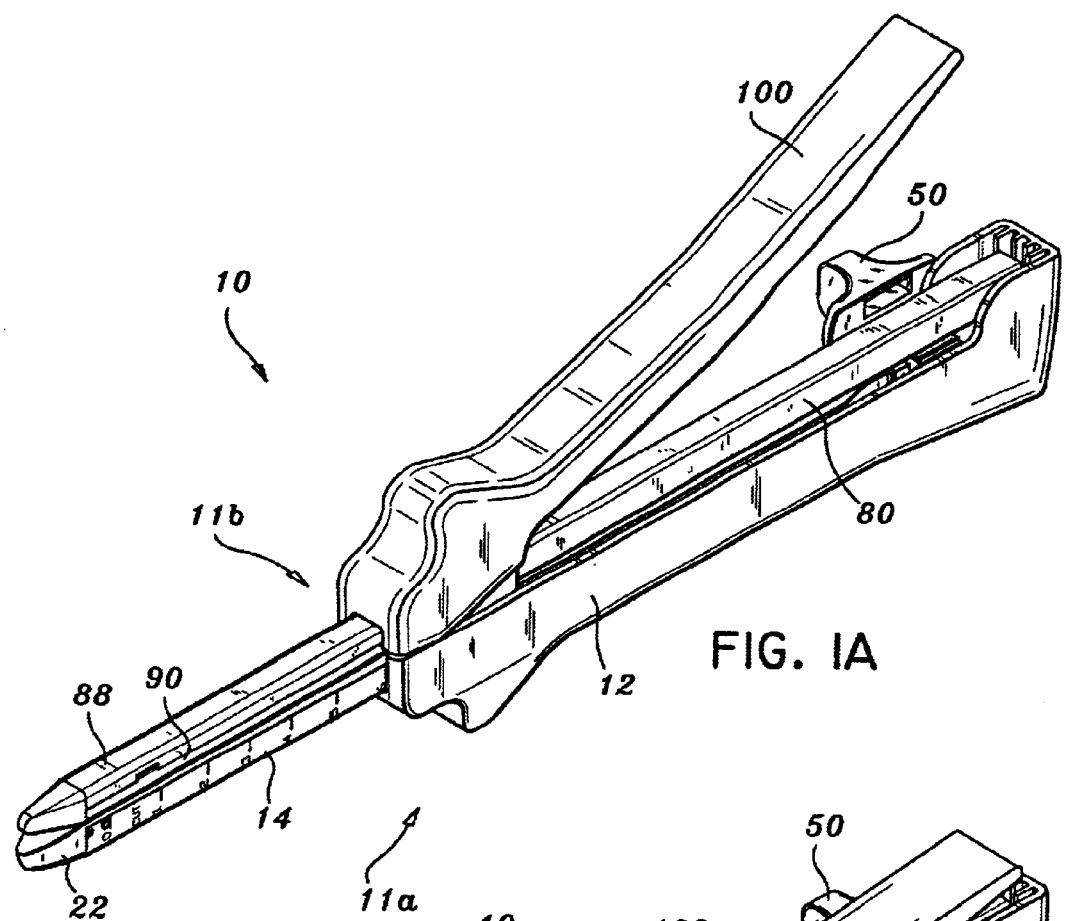
FIG. IA
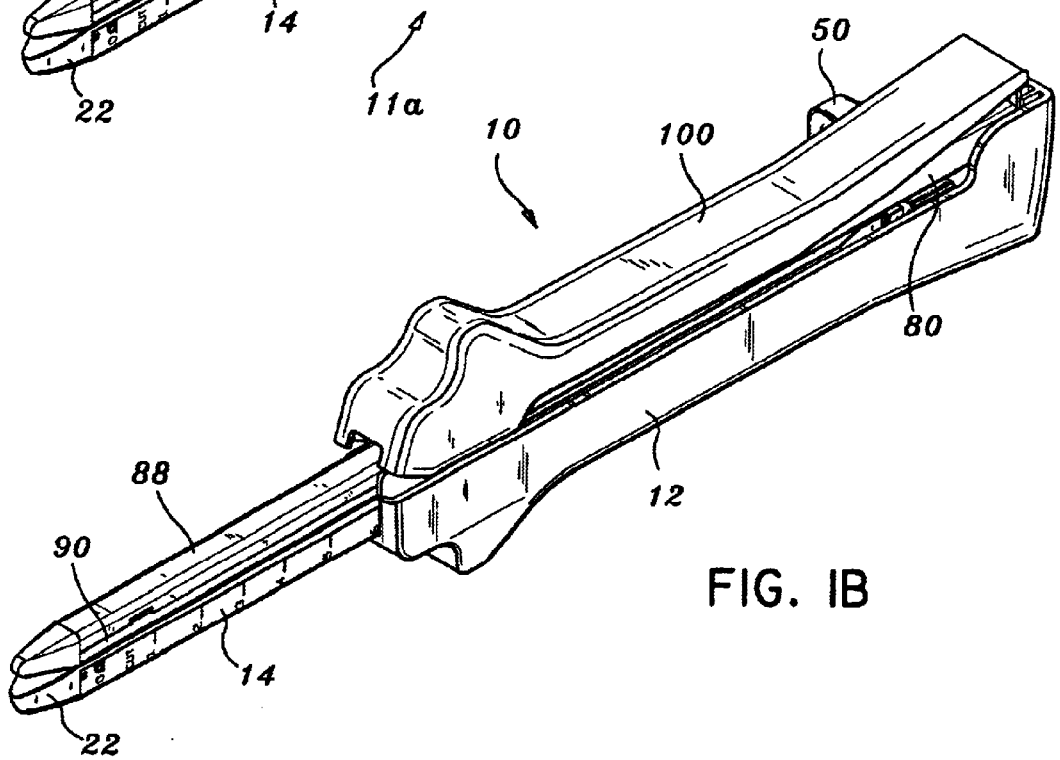
FIG. IB

SURGICAL STAPLER

This application is a Continuation of U.S. patent application Ser. No. 09/366,583, which was filed on Aug. 4, 1999, now U.S. Pat. No. 6,202,919, which is a Division of U.S. patent application Ser. No. 08/549,580, filed Oct. 27, 1995 now U.S. Pat. No. 5,941,442 and are herein incorporated by reference.

BACKGROUND

1. Technical Field

This application relates to surgical staplers, and more particularly, to an apparatus for sequentially applying a plurality of surgical fasteners to body tissue.

2. Background of Related Art

Surgical devices wherein tissue is first grasped or clamped between opposing jaw structure and then joined by means of surgical fasteners are well known in the art. In some instruments a knife is provided to cut the tissue which has been joined by the fasteners. The fasteners are typically in the form of surgical staples however, two part polymeric fasteners are also utilized.

Instruments for this purpose can comprise two elongated members which are respectively used to capture or clamp tissue. Typically, one of the members carries a cartridge which houses a plurality of staples arranged in at least two lateral rows while the other member comprises an anvil which defines a surface for forming the staple legs as the fasteners are driven from the cartridge. Where two part fasteners are used, this member carries the mating part, e.g. the receiver, to the fasteners driven from the cartridge. Generally, the stapling operation is effected by a pusher which travels longitudinally through the cartridge carrying member, with the pusher acting upon the staples to sequentially eject them from the cartridge. A knife may travel with the pusher between the staple rows to longitudinally cut and/or open the stapled tissue between the rows of staples. Such instruments are disclosed in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of staplers are disclosed in U.S. Pat. Nos. 4,429,695, 5,065,929, and 5,156,614.

Many of the prior art linear stapling devices discussed above include a significant number of moving parts, small components and machined structural elements that are costly to fabricate and time consuming to assemble. These factors add to the overall cost of the stapling devices and thus increase the costs incurred by hospitals and health care professionals, and ultimately, the patient upon which the devices are utilized. A linear stapler that could be manufactured and assembled less expensively would provide great benefits.

SUMMARY

The subject application is directed to a linear surgical stapler that is constructed from fewer, less expensive components than known prior art staplers configured to sequentially apply a plurality of surgical staples to body tissue. The stapler includes a first body portion supporting an anvil plate which defines a fastener forming surface and a second body portion configured to releasably mate with the first body portion. In the detailed description which follows, the first and second body portions of the stapler are also referred to as the "anvil half-section" and "cartridge half-section", respectively.

A disposable loading unit is removably supported in the second body portion and includes a cartridge defining a plurality of slots and a tissue contacting surface, a plurality of surgical fasteners disposed in the slots of the cartridge, a plurality of ejectors or pushers positioned adjacent the surgical fasteners. A wedged actuator provided in the disposable loading unit is positioned and configured to enter and translate through the cartridge to sequentially interact with the pushers.

The stapler in a preferred embodiment, further includes an elongated actuation member mounted for longitudinal movement within the second body portion and releasably engagable with the wedged actuator, whereby longitudinal movement of the actuation member causes the wedged actuator to interact with the ejectors, driving the surgical fasteners from the cartridge to be formed against the anvil plate.

The first body portion preferably includes an elongate anvil support member and a pivoting lever handle. The anvil plate is preferably formed separate from the anvil support member and includes a plurality of staple forming pockets defining the anvil forming surface. The anvil plate also includes means for engaging the anvil support member during assembly of the surgical stapler to securely fasten the anvil plate to the support member. A notched area is defined adjacent a proximal end of the anvil support member and correspondingly positioned detents are formed adjacent a proximal end of the second body portion. The notched area and the detents cooperate to facilitate relative pivotal movement of the first and second body portions when they are mated with one another.

Preferably, a pair of upstanding flanges are formed on the disposable loading unit proximal of the tissue contacting surface thereof. The flanges define a structural tissue stop to limit the movement of body tissue. The flanges are also dimensioned to engage a pair of corresponding apertures formed in the anvil plate to maintain the first and second body portions in alignment with one another when the surgical stapler is in a closed or clamped position.

The wedged actuator of the disposable loading unit is preferably monolithically formed from a planar piece of sheet metal during a stamping process and includes a planar base and a pair of upstanding parallel cam wedges. An upturned flange is formed at a distal end of the actuation member for releasably engaging a complementary slot formed in the base of the wedged actuator. The wedged actuator preferably further includes an upstanding support flange to which a knife blade is fastened. The knife blade is provided to form an incision in the stapled body tissue.

A retaining channel depends from a distal end of the second body portion for supporting the disposable loading unit. Preferably, the disposable loading unit and the retaining channel include complementary engagement structures for releasably securing the disposable loading unit in the retaining channel. Opposed bearing structures are formed in the retaining channel at a proximal end thereof for abutting the anvil support beam when body tissue is clamped between the anvil plate and the tissue contacting surface of the cartridge. The bearing structures serve to inhibit the anvil support beam from bending as a result of the compressive forces generated during clamping.

Further features of the surgical apparatus of the subject application will become more readily apparent to those skilled in the art from the following detailed description of the apparatus taken in conjunction with the drawings.

BRIEF DESCRIPTION OF THE DRAWINGS

Various embodiments of the surgical stapling apparatus of the subject application will be described hereinbelow with reference to the drawings wherein:

FIG. 1A is a perspective view of a surgical stapling apparatus constructed in accordance with a preferred embodiment with the clamping handle thereof disposed in an upright open position;

FIG. 1B is a perspective view of the surgical stapling apparatus illustrated in FIG. 1A with the clamping handle disposed in a closed position;

DETAILED DESCRIPTION OF PREFERRED EMBODIMENTS

Figure 2:
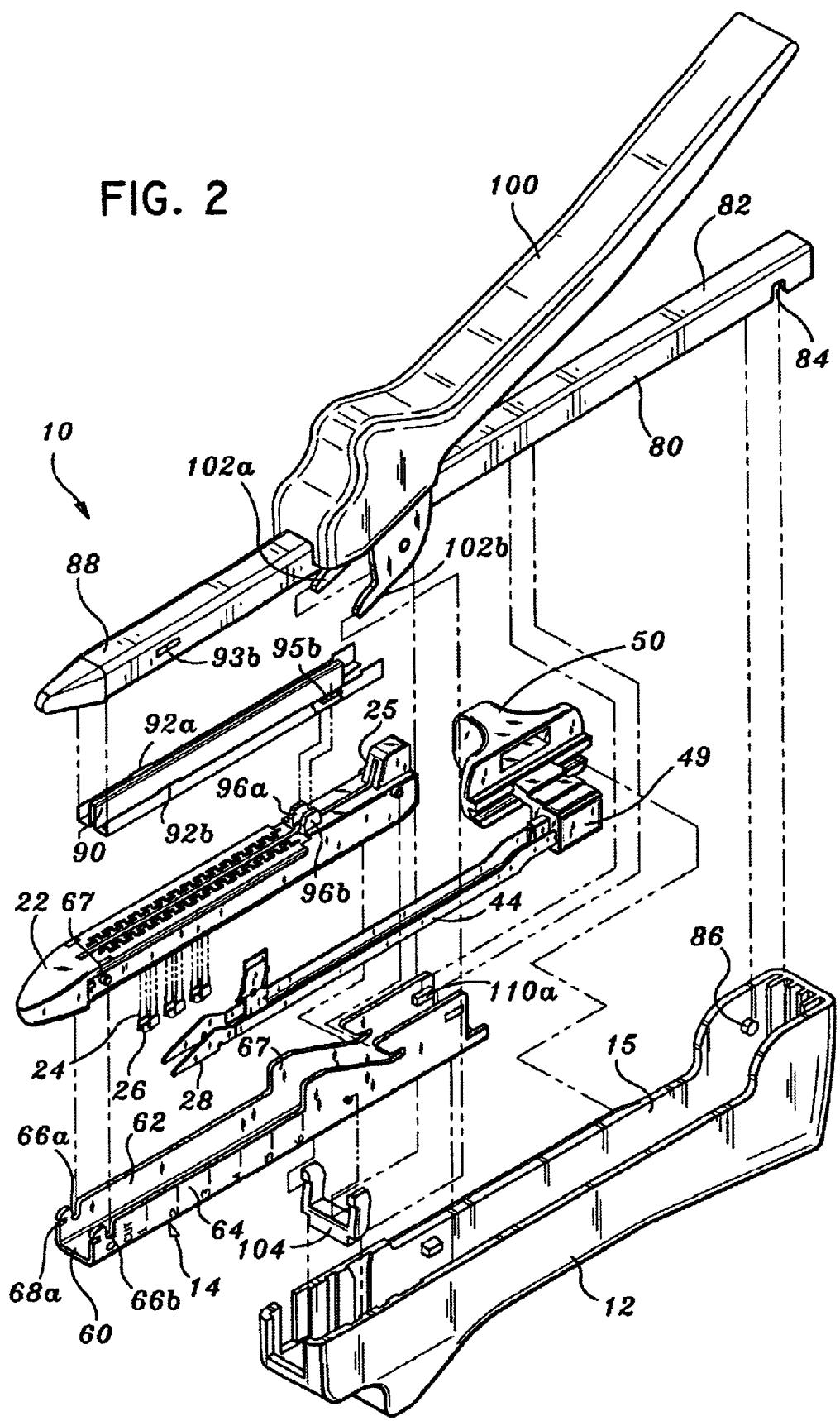
FIG. 2 is an exploded perspective view of the surgical stapling apparatus of FIGS. 1A and 1B.

In the drawings and in the description which follows, the term "proximal", as is traditional, will refer to the, end of the apparatus which is closer to the operator, while the term "distal" will refer to the end of the apparatus which is further from the operator.

Referring now to the drawings wherein like reference numerals identify similar structural elements, there is illustrated in FIGS. 1A and 1B a surgical stapling device constructed in accordance with a preferred embodiment and designated generally by reference numeral 10 which includes a cartridge half section 11A and an anvil half section 11B. As will become readily apparent to those having ordinary skill in the art, surgical stapler 10 is constructed in such a manner so as to substantially reduce the costs associated with its fabrication and assembly as compared to prior art linear staplers.

Figure 3:
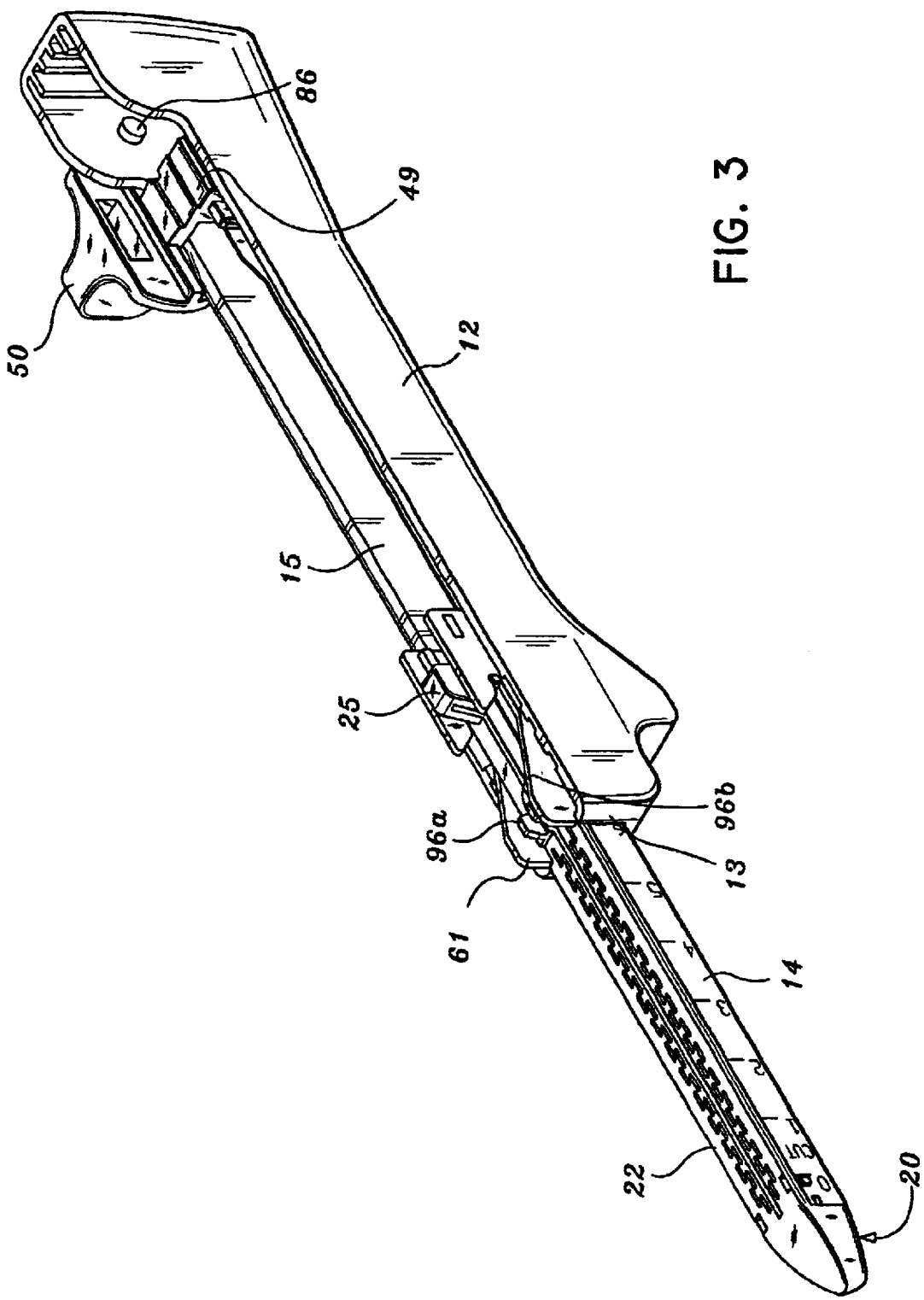
FIG. 3 is a perspective view of the lower body portion of the surgical stapling apparatus of FIGS. 1A and 1B.
Figure 4A:
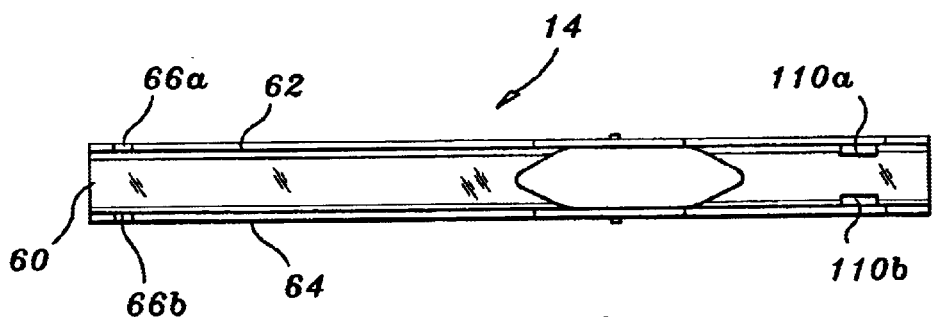
FIG. 4A is a top plan view of the retention channel of the surgical stapling apparatus of FIGS. 1A and 1B.
Figure 4B:
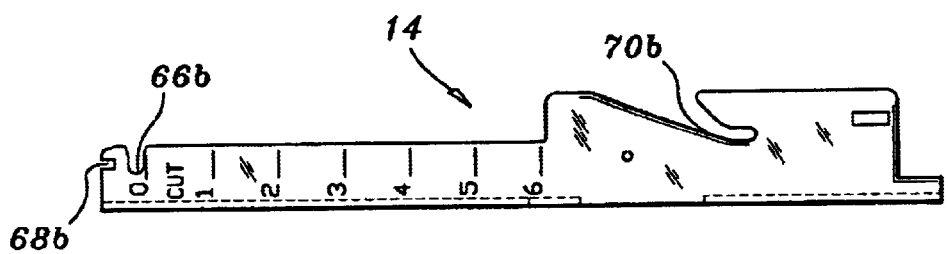
FIG. 4B is a side elevational view of the retention channel shown in FIG. 4A.
Figure 4C:
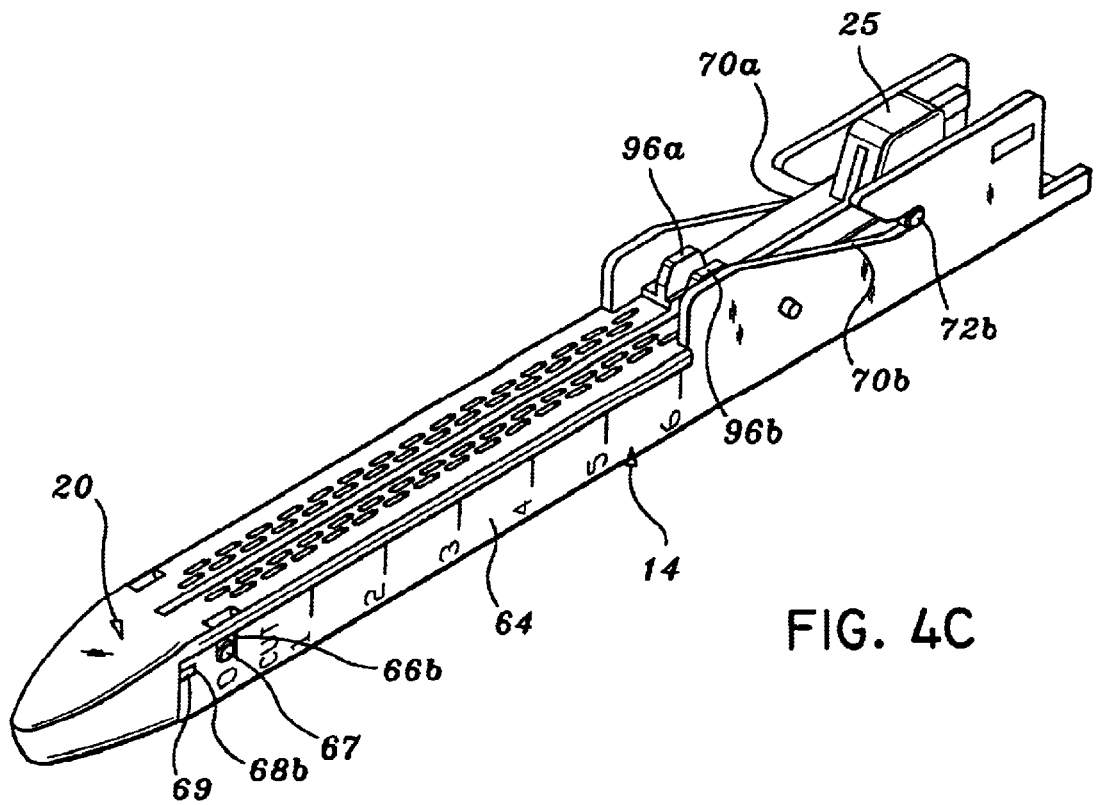
FIG. 4C is a perspective view of the retention channel of FIGS. 4A and 4B with the disposable loading unit retained therein.

Referring to FIGS. 2 and 3, surgical stapler 10 includes a body portion 12 defining a handle for grasping and supporting the device. A retaining channel 14 is mounted in the interior cavity 15 of body portion 12 adjacent the distal end thereof. Retaining channel 14 is dimensioned and configured to support a disposable loading unit 20, as illustrated in FIG. 4C.

Figure 5:
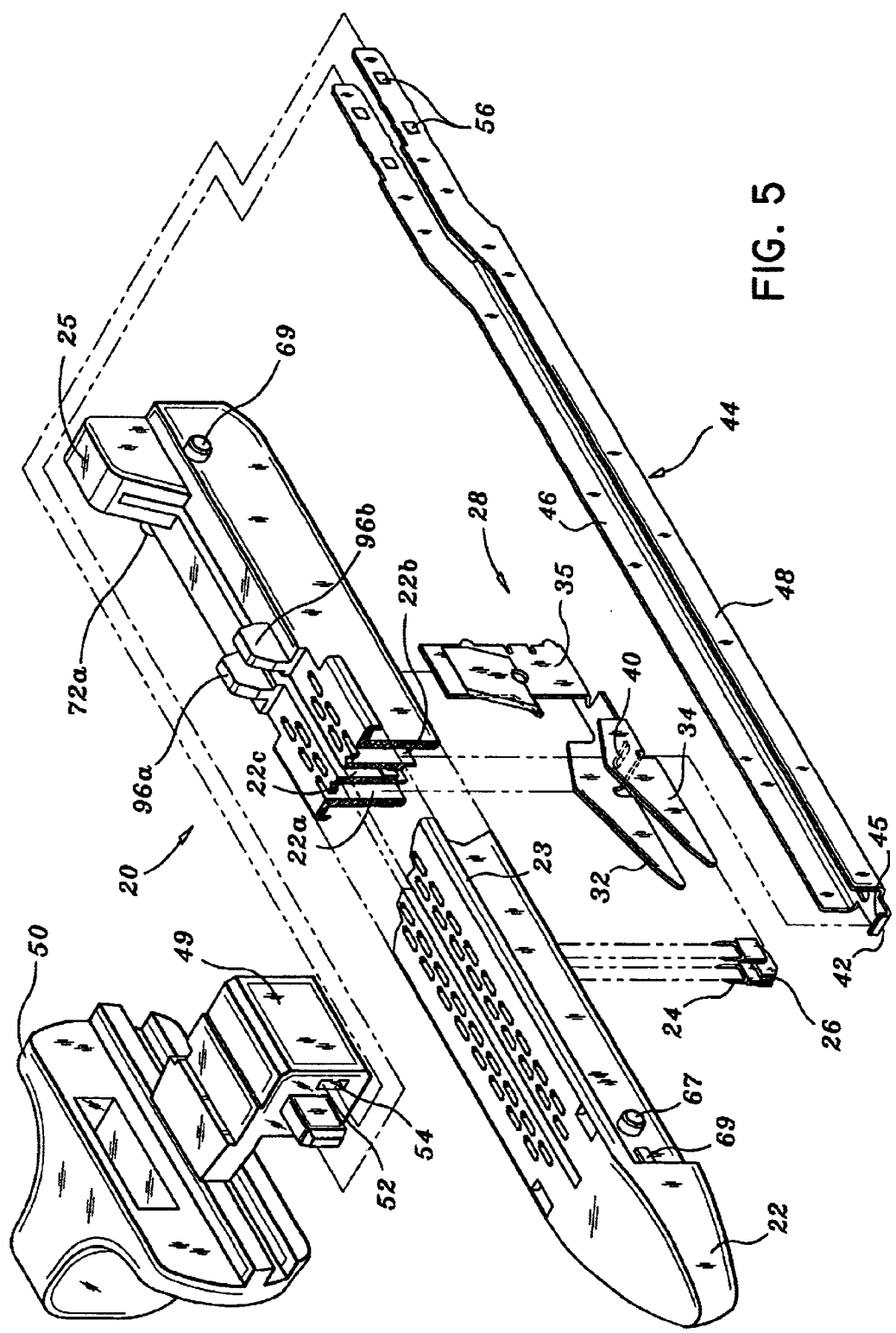
FIG. 5 is an enlarged perspective view, with parts separated for ease of illustration, of the disposable loading unit and actuation assembly of the surgical stapling apparatus of the subject application.
Figure 5A:
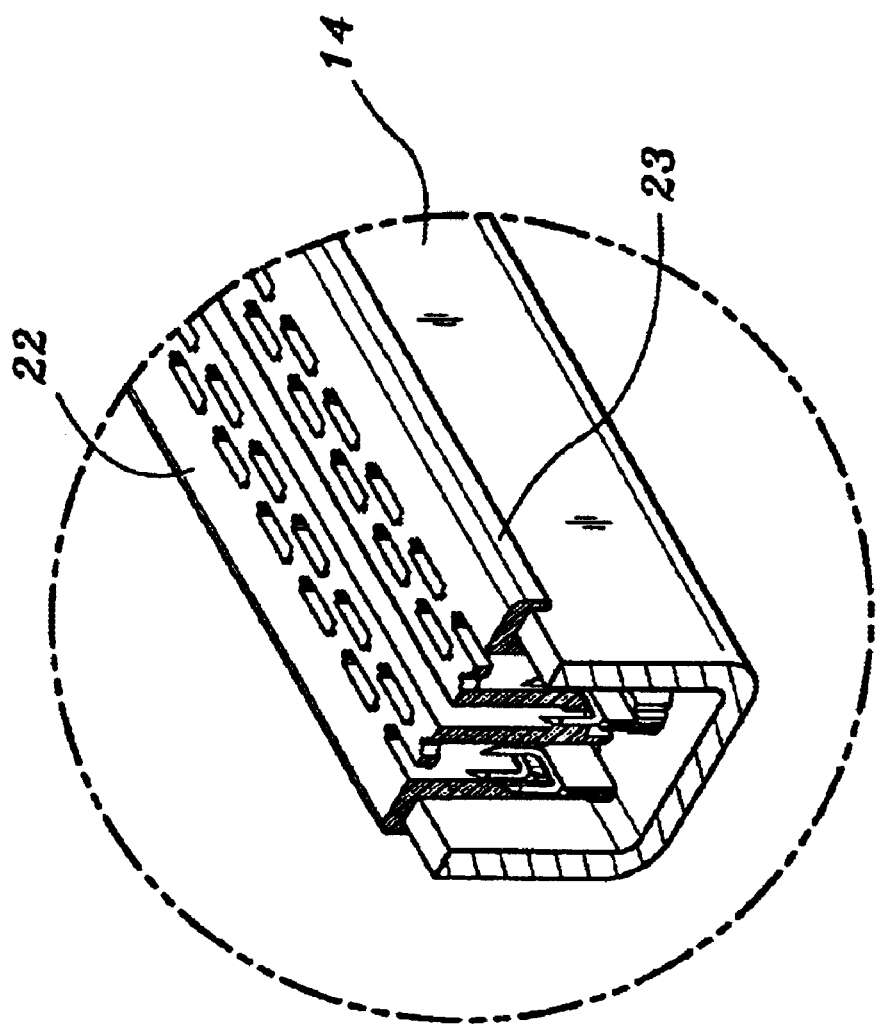
FIG. 5A is a cross-sectional view showing the engagement of the cartridge lip and the retention channel.

As shown in FIG. 5, the disposable loading unit 20 includes a cartridge 22 having a plurality of slots which support a corresponding number of surgical staples 24, a plurality of staple pushers or ejectors 26 adapted and configured to eject the staples from the slots when acted upon by a staple driving force, and an actuation sled 28 which is mounted to translate through cartridge 22 in a longitudinal direction to transmit a staple driving force to the ejectors. The cartridge is preferably composed of liquid crystal polymer material; although other materials are contemplated. The cartridge 22 has a lip 23 which engages the retention channel 14 to prevent inward rotation of the cartridge (see FIG. 5A).

Figure 6A:
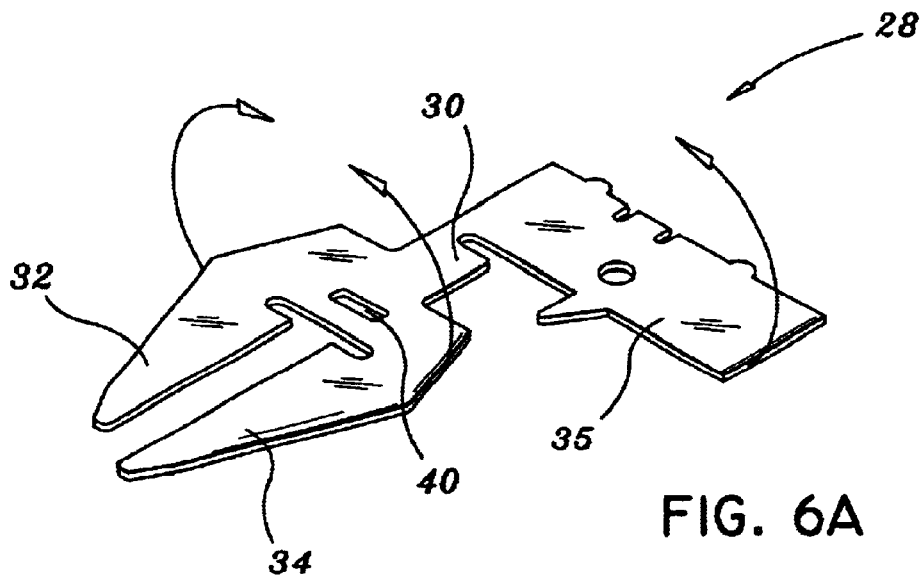
FIG. 6A is a perspective view of the actuation sled of the disposable loading unit shown in FIG. 5 in a pre-formed condition.
Figure 6B:
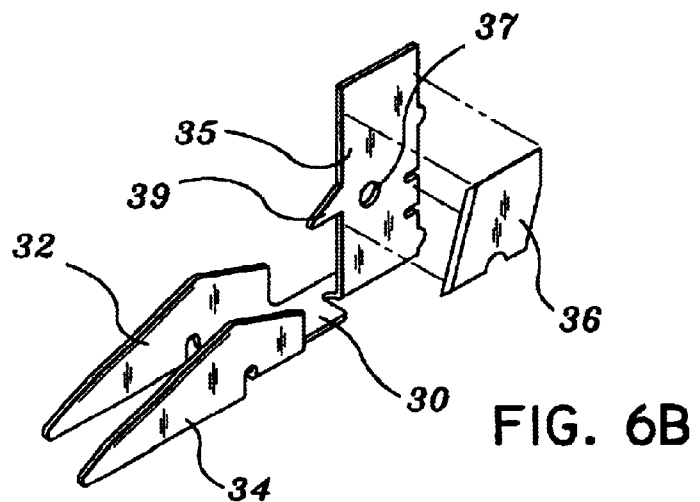
FIG. 6B is a perspective view of the actuation sled shown in FIG. 6A in a formed condition with the knife blade separated therefrom for illustrative purposes.
Figure 6C:
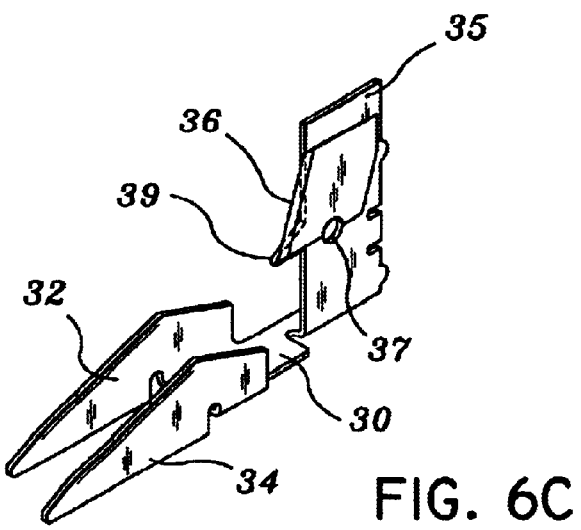
FIG. 6C is a perspective view of the formed actuation sled shown in FIG. 6B with the knife blade mounted to the blade support portion thereof.

As best seen in FIG. 6A, actuation sled 28 is preferably monolithically formed from a single piece of sheet metal or a similar material which is folded into the desired structural configuration shown in FIG. 6C. In this configuration, actuation sled (staple actuator) 28 defines a base portion 30, two upstanding cam wedges 32 and 34, and an upstanding shank 35 which supports a knife blade 36. Knife blade 36 is preferably spot welded to shank 35, although other known fastening methods may be employed. As illustrated in FIG. 6B, a weldment port 37 and a winglet 39 are provided to facilitate the proper alignment and cohesion of knife blade 36 to shank 35 during fabrication. Cam wedges 32 and 34 are staggered with respect to one another so that one leads the other throughout the sled's translation through cartridge 22. In doing so, the staple driving forces within cartridge 22 remain balanced during a staple driving operation. Longitudinal slots 22a and 22b accommodate the longitudinal translation of cam wedges 32 and 34, while slot 22c accommodates the longitudinal translation of shank 35 (see FIG. 5). Although illustrated with a knife, it is also contemplated that the apparatus can be provided without a knife bade and therefore would staple tissue without making an incision.

The base portion 30 of actuation sled 28 has a transverse slot 40 defined therein which is dimensioned and configured to releasably retain an upturned flange 42 formed at the distal end of elongated actuation channel 44 (FIG. 5). When the disposable loading unit 20 is placed into retaining channel 14 and actuation sled 28 is disposed in its proximal-most position, flange 42 releasably engages slot 40. Thus, movement of actuation channel 44 moves actuation sled 28. After a stapling operation, when the disposable loading unit is removed from the retaining channel, flange 42 is easily disengaged from slot 40.

With continued reference to FIG. 5, actuation channel 44 is defined by a base portion 45 and two parallel upstanding beams 46 and 48 of elongate configuration. The distal ends of beams 46 and 48 are staggered to match the staggered orientation of cam wedges 32 and 34, respectively. The proximal end of each beam projects rearwardly to engage the mounting block 49 that is associated with firing knob 50. A pair of slots 52 (only one of which is shown) are formed in mounting block 49 for receiving the proximal end of each of the upstanding beams 46, 48 of actuation channel 44 and the slots are provided with detents 54 for engaging apertures 56 in the beam ends to lockingly retain the beams in mounting block 49. In use, longitudinal movement of firing knob 50 causes corresponding longitudinal translation of actuation channel 44 and actuation sled 28.

Referring to FIGS. 2 and 4C, retention channel 14 includes a base portion 60 and two upstanding parallel walls 62 and 64. Numerical indicia is imprinted on the walls 62, 64 of retention channel 14 to indicate the length of the staple line. Retention structures are provided at the distal end of each of the walls 62, 64 to engage corresponding structures provided on the disposable loading unit 20. In particular, notches 66a and 66b are provided for engaging corresponding protuberances, such as protuberance 67, and slots 68a and 68b are provided for engaging corresponding detents, such as detent 69. These structures inhibit lateral, longitudinal and perpendicular shifting of the cartridge 22 (and disposable loading unit 20) within the retaining channel 14. Ramped engagement slots 70a and 70b are also defined in the opposed walls of retention channel 14 for interacting with a pair of opposed protuberances 72a and 72b (FIG. 5) to guide the disposable loading unit 20 into retention channel 14 when loaded into surgical stapler 10.

Referring again to FIG. 2, surgical stapler 10 further includes an elongate anvil support beam 80 which has a generally U-shaped cross-sectional configuration. Anvil support beam 80 and its associated structures are also referred to herein as the "anvil half-section". The distal end portion 88 of the anvil support beam 80 in one embodiment is tapered in height h in a distal direction to provide additional support and reduce deflection during a staple firing operation. The proximal end portion 82 of support beam 80 has a notched area 84 for engaging a pair of corresponding detents 86 (only one of which is shown), which extend into the cavity 15 of body portion 12 adjacent the proximal end thereof. The detents 86 are engaged when the cartridge half-section 11a and anvil half-section 11b are mated with one another. The distal end portion 88 of anvil support beam 80 is configured to support a preformed anvil plate 90 against which staples are driven and formed during a stapling procedure.

Figure 7:
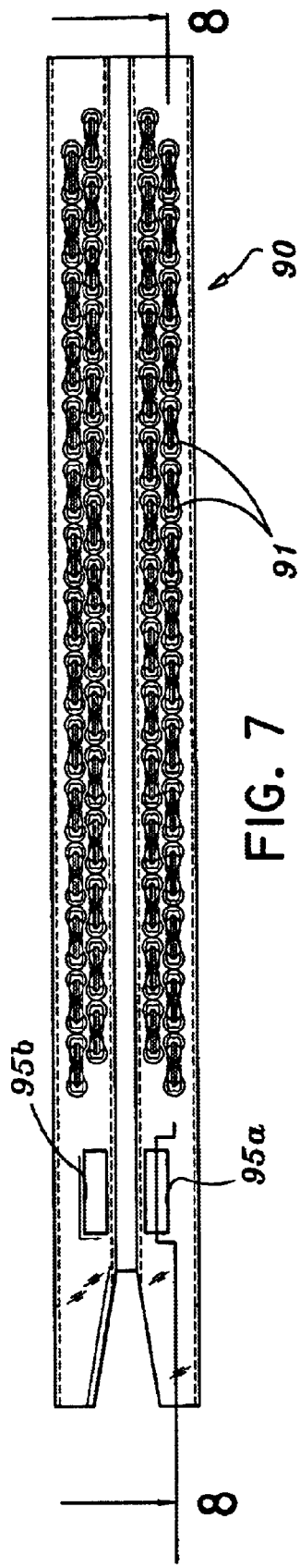
FIG. 7 is a plan view of the preformed anvil plate which is mounted to the anvil support beam of the upper body portion of the stapling apparatus shown in FIGS. 1A and 1B.
Figure 8:
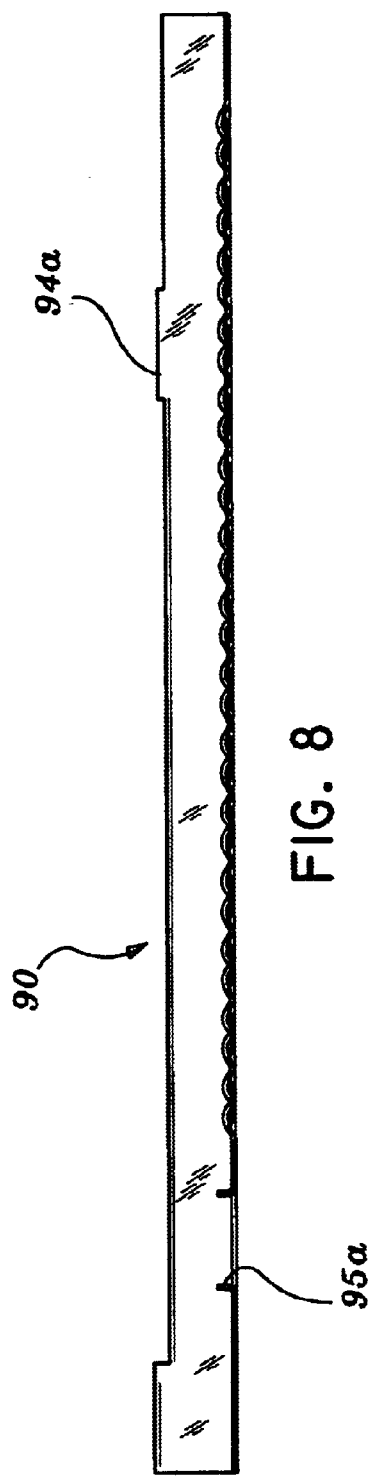
FIG. 8 is a cross-sectional view of the preformed anvil plate taken along line 8—8 of FIG. 7.
Figure 9:
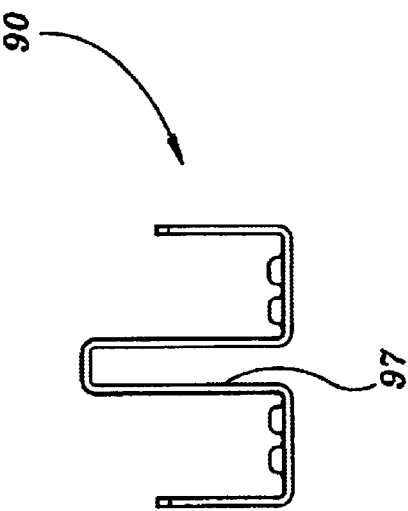
FIG. 9 is a front end view of the preformed anvil plate illustrated in FIGS. 7 and 8.
Figure 10:
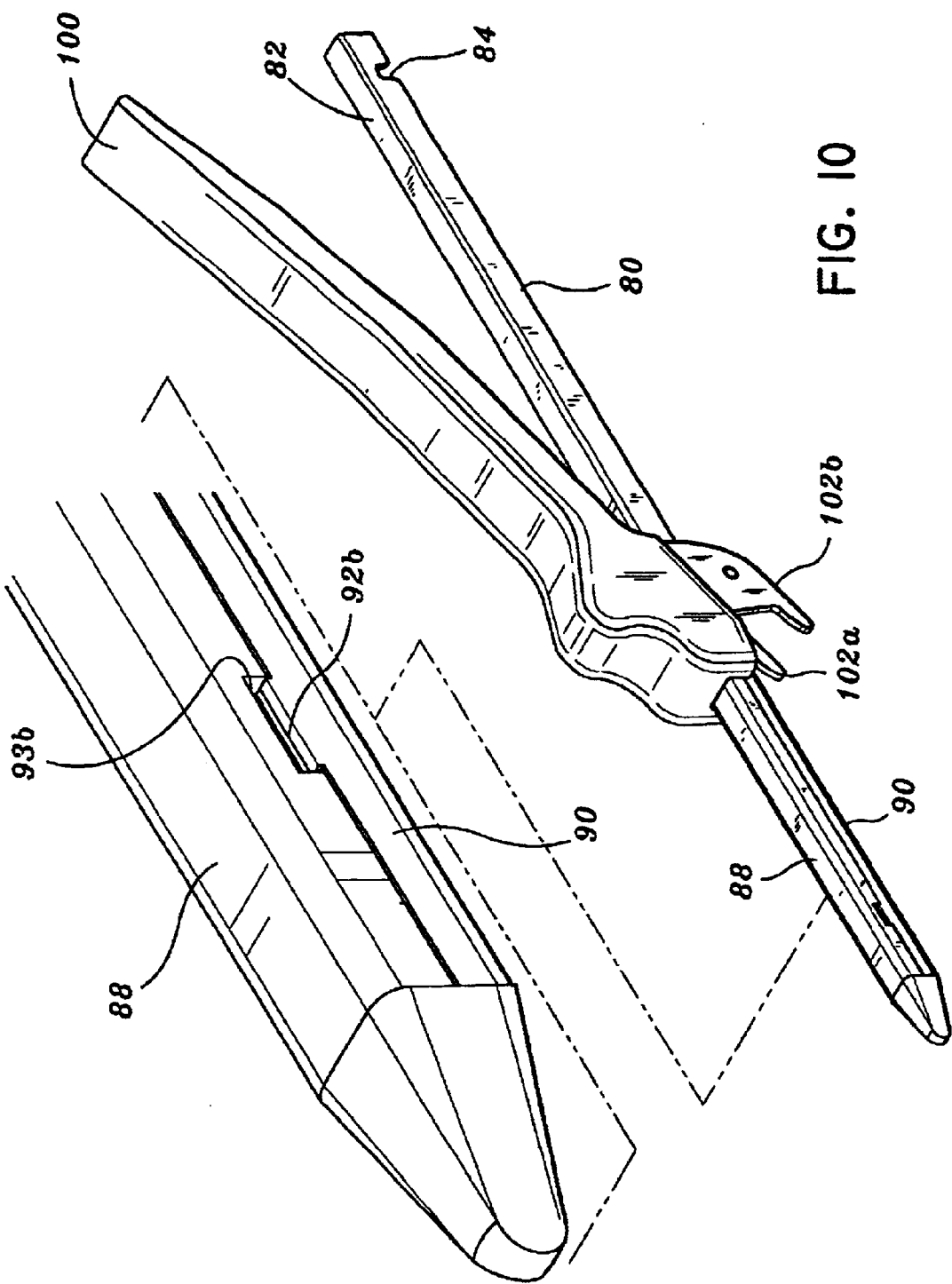
FIG. 10 is a perspective view of the upper body portion of the surgical stapling apparatus of FIGS. 1A and 1B with an enlarged localized view of a distal portion thereof illustrating the connective engagement between the anvil plate and the anvil support beam.

Referring to FIGS. 7 and 8, anvil plate 90 is formed from a unitary piece of metal and is cold formed and stamped to define a plurality of staple forming recess or cups 91. Each staple forming recess corresponds to a particular staple housed within cartridge 22. Anvil plate 90, as shown in FIG. 2, is provided with two opposed tangs 92a and 92b which extend inwardly to engage complementary engagement slots 93b (only one is shown) in anvil support beam 80 during fabrication and assembly (see FIG. 10). The cross-sectional configuration of anvil plate 90 is dimensioned to complement the cross-sectional geometry of support beam 80 (see FIG. 9). More particularly, the cavity 97 which extends along the length of the anvil plate 90 corresponds to a similar channel formed in support beam 80. These areas accommodate shank 35 and knife blade 36 as it translates distally to form an incision in stapled body tissue during a stapling operation.

A pair of rectangular apertures 95a and 95b are formed in anvil plate 90 adjacent the proximal end thereof for receiving a pair of correspondingly positioned flanges 96a and 96b which project upwardly away from the tissue contacting surface (see FIGS. 2 and 4C). The interaction between aperture 95a, 95b and flanges 96a, 96b ensures that the cartridge 22 and the anvil plate 90 are properly aligned with one another during a stapling procedure. Flanges 96a, 96b are spaced proximally of tissue stop portion 61 of retention channel 14. Portion 61 and the distal edge 13 of handle portion, best seen in FIG. 3, cooperate to prevent tissue from extending proximally.

Referring again to FIG. 2, the anvil half-section of surgical stapler 10 further includes clamping handle 100 which is used to securely clamp tissue between the staple forming surface of anvil plate 90 and the tissue contacting surface of cartridge 22. Clamping handle 100 is pivotably mounted to anvil support beam 80 about a transverse pivot pin which is not shown in the drawings. A pair of clamping hooks 102a and 102b depend from clamping handle 100 for interacting with the U-shaped clamping beam 104 supported within the internal cavity defined in handle portion 12.

When stapler 10 is assembled prior to use, the notched area 84 at the proximal end 82 of anvil support beam 80 is engaged with the cooperating detents 86 in the inner cavity 15 of body portion 12. Thereupon, the anvil half-section is mated with the cartridge half-section, and clamping handle 100 is disposed in the upright unclamped position shown in FIG. 1A. Subsequently, when body tissue is properly disposed between the staple forming surface of anvil plate 90 and the tissue contacting surface of cartridge 22, the anvil half section is pivoted toward the cartridge half section, about the detents in body portion 12, such that the distal ends of clamping hooks 102a and 102b are positioned immediately adjacent the proximal end of the base of U-shaped clamping beam 104. Concomitantly, flanges 96a and 96b engage apertures 95a and 95b in anvil plate 90 to ensure proper alignment of the anvil and the cartridge.

Then, to securely clamp the captured body tissue, clamping handle 100 is pivoted from the position illustrated in FIG. 1A to that which is shown in FIG. 1B. At such a time, clamping hooks 102a and 102b engage the base of clamping beam 104, locking the stapler in a clamped condition. During clamping, the captured body tissue exerts a counterforce against the tissue contacting surface of cartridge 22 and the fastener forming surface of the anvil plate 90, urging the two structures apart. To overcome these forces and prevent the proximal portion 82 of anvil support beam 80 from bending, bearing surfaces are defined within the retention channel 14 to support the compressive forces generated during clamping. In particular, as illustrated in FIG. 4A, opposed bearing shelves 110a and 110b are stamp formed in the opposed walls 62 and 64 of retention channel 14. The bearing shelves are positioned to abut the medial section of anvil support beam 80 proximate the clamping handle pivot point.

Figure 11:
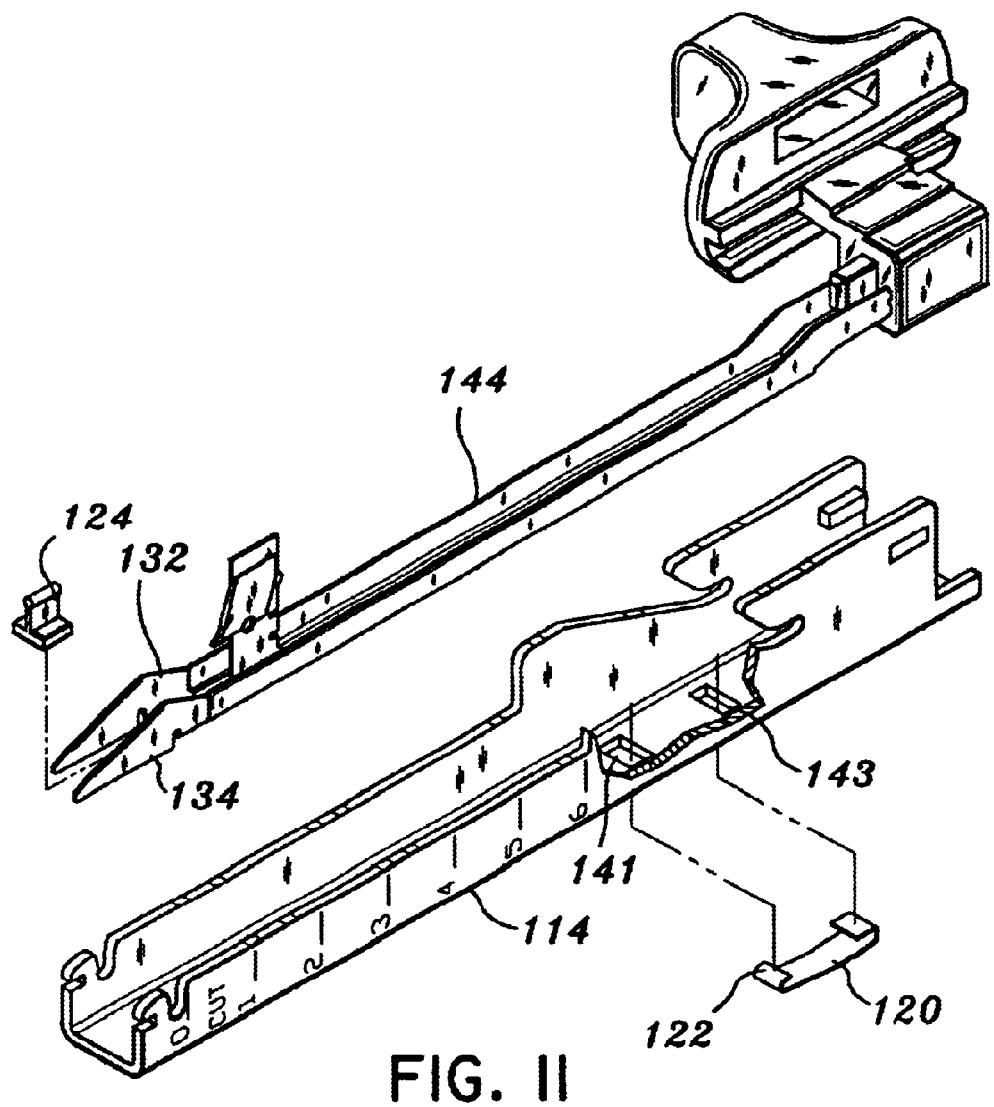
FIG. 11 is an exploded perspective view of an embodiment utilizing a lockout mechanism to prevent reactuation of the apparatus.
Figure 11A:
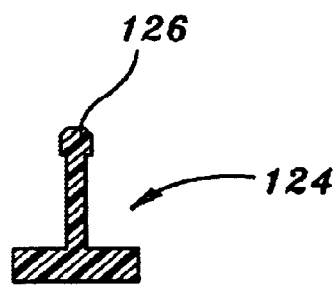
FIG. 11A is an enlarged cross-sectional view of the T-shaped member of the lockout mechanism.
Figure 12:
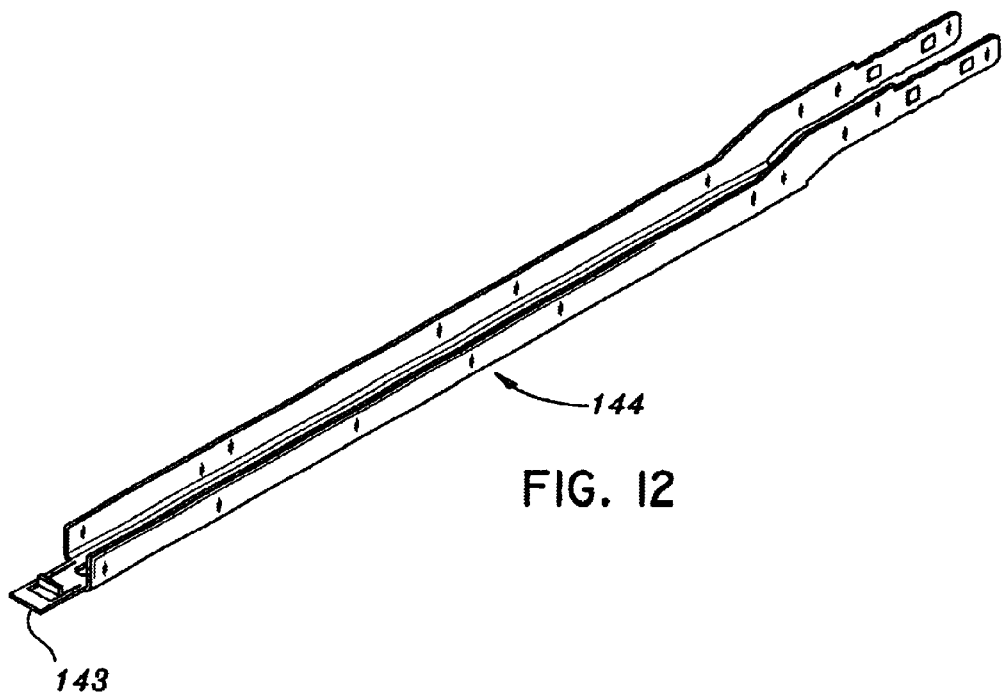
FIG. 12 is an enlarged perspective view of the actuation channel having an edge for engagement by the hook of the lockout mechanism.
Figure 13:
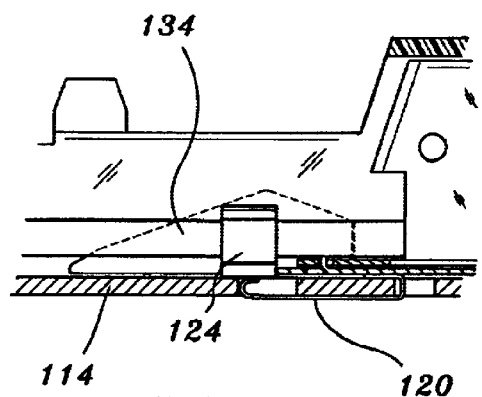
FIGS. 13 and 13A are side views of the lockout mechanism illustrating its movement from a non-engaged to an engaged position.
Figure 13A:
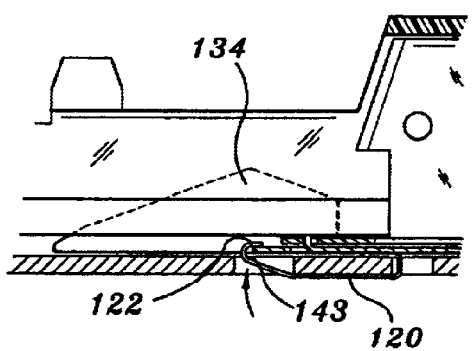

It may also be desirable to provide a locking mechanism to prevent reactuation of the apparatus after it has been actuated. For example, a locking member 120 shown in FIG. 11 can be positioned in the retaining channel 114. The locking member 120 is biased to an upward engagement position and each end extends through a window 141, 143 in the channel 114. A T-shaped member 124 is positioned between the cam wedges 132, 134 to bias the hook portion 122 out of engagement with the actuation channel 144. Head portion 126 of T-shaped member 124 (FIG. 11A) is initially retained in the cartridge by a pair of detents in the cartridge which extend into the knife slot. When the stapler is actuated, head portion 126 of T-shaped member 124 in the knife slot. A second pair of detents (not shown) at the distal end of the knife slot engages head portion 126 of T-shaped member 124 to hold it at the distal end of cartridge 122 when the cam wedges 132, 134 are advanced to the distal position. When actuation channel 144 is retracted from the post-actuated position to the pre-actuated position, the T-shaped member 124 remains forward allowing hook portion 122 to return to the upward position and extend through the window 141 in retaining channel 114 to engage edge 143 (see FIGS. 12 and 13A) of actuation channel 144 to prevent advancement of the actuation channel. FIGS. 13A, 13B illustrate movement of the locking member 120 from an initial non-engaged position (FIG. 13A) out of engagement with actuation channel 144 to an engaged position (FIG. 13B) in engagement with actuation channel 144 to prevent distal movement thereof.

Figure 14:
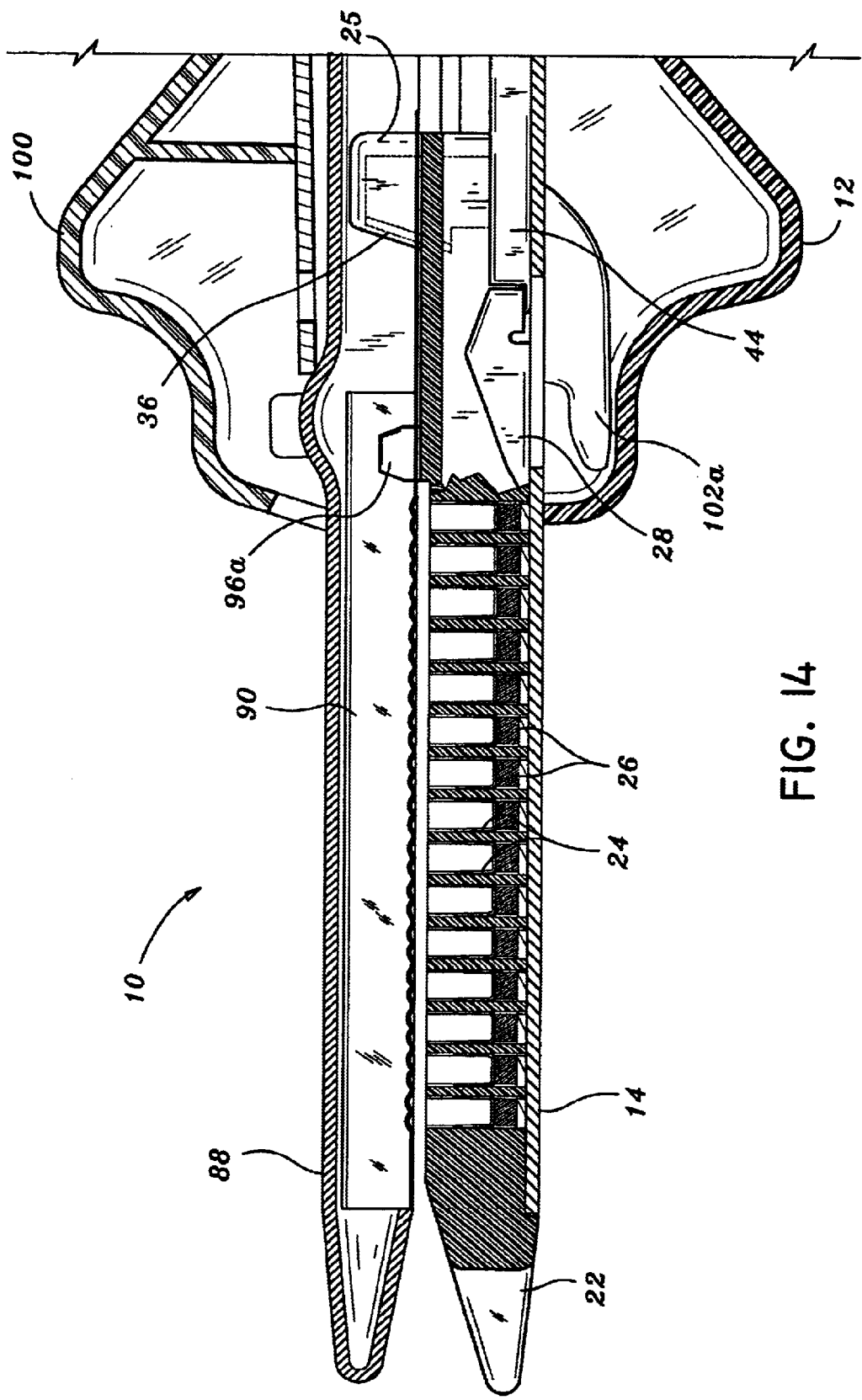
FIG. 14 is a side elevational view in cross-section of the surgical stapling apparatus of the subject application with the actuation sled disposed in a pre-actuated proximal position.
Figure 15:
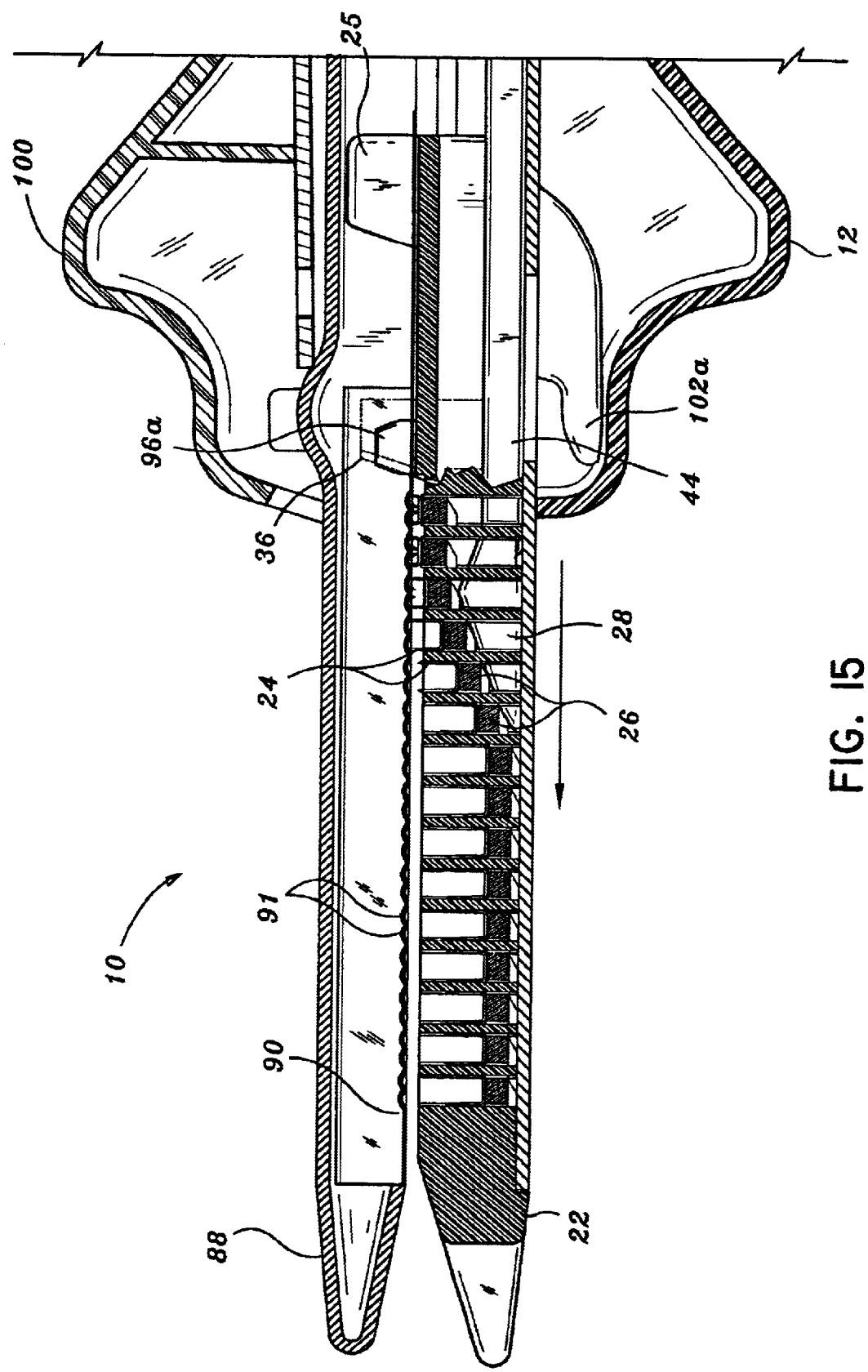
FIG. 15 is a side elevational view in cross-section of the surgical stapling apparatus of the subject application with the actuation sled disposed in a partially advanced position.
Figure 16:
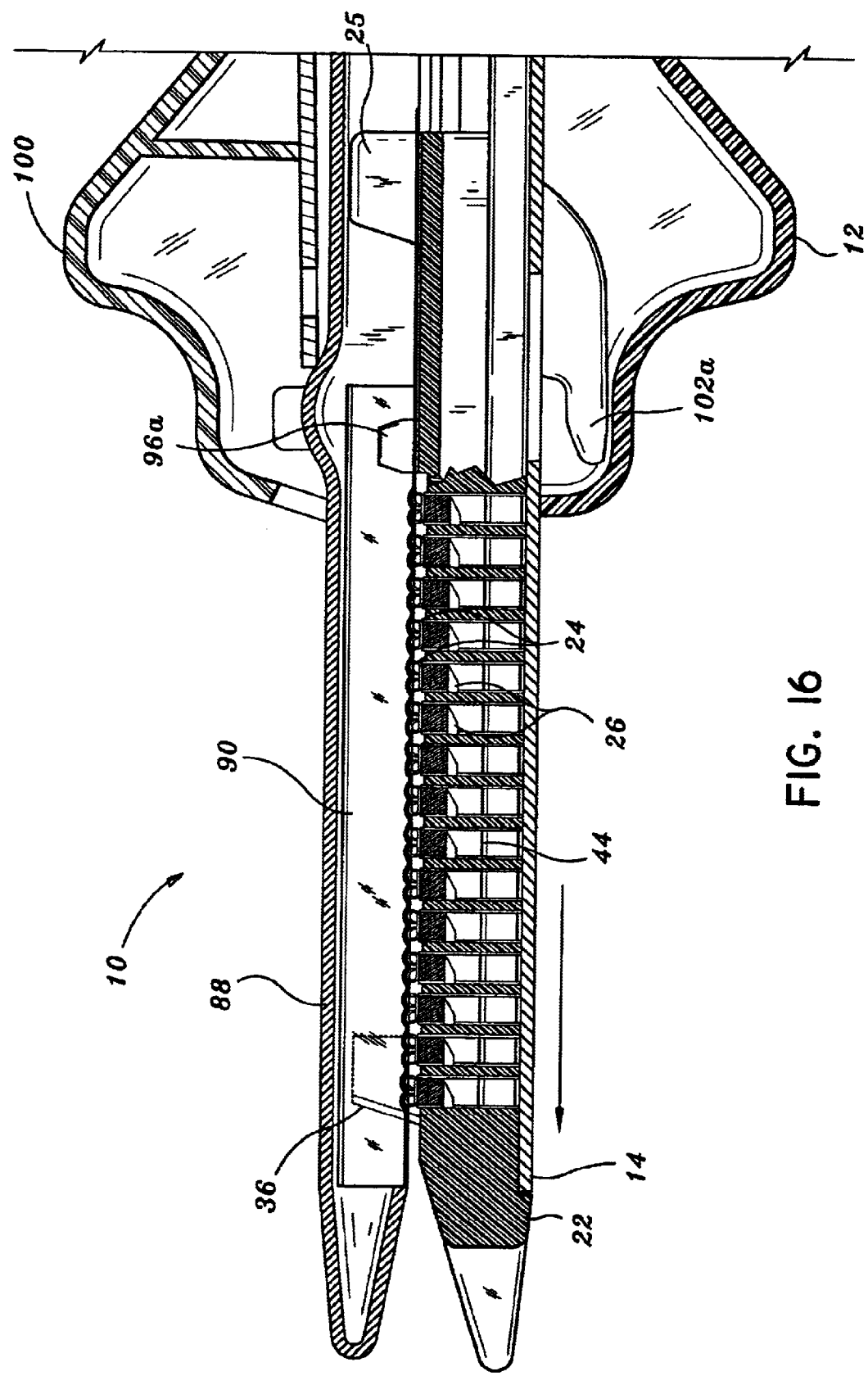
FIG. 16 is a side elevational view in cross-section of the surgical stapling apparatus of the subject application with the actuation sled advanced to the distal end of the cartridge at the conclusion of a staple firing procedure.

Referring now to FIGS. 14–16, there is illustrated, in sequential order, a staple firing operation in which a plurality of staples are ejected from cartridge 22 and driven against the staple forming surface of anvil plate 90. In operation, prior to firing surgical stapler 10, actuation sled 28 is in the proximal-most position shown in FIG. 14. At such a time, knife blade 36 is enclosed in a protective housing 25 formed adjacent the proximal end of disposable loading unit 20. To fire the apparatus, firing knob 50 is moved in a distal direction. Accordingly, as illustrated in FIG. 15, actuation channel 44 drives actuation sled 28 distally into and through cartridge 22. During its distal translation, the angled leading surfaces of cam wedges 32 and 34 sequentially contact ejectors 26, urging them in a direction transverse to the direction of movement of actuation sled 28. As a result, the ejectors 26 push the staples 24 from their individual slots, driving each staple into a respective staple forming cup 91 in anvil plate 90.

Sequential firing of the staples continues until actuation sled 28 is advanced to the distal end of cartridge 22, at which time, all of the staples once housed within the cartridge 22 will have been ejected (see FIG. 16). Thereafter, the firing knob 50 is retracted to its original position, the cartridge and anvil sections are separated, and the spent disposable loading unit 20 is removed from retaining channel 14. Subsequently, a new, fully loaded disposable loading unit can be positioned in retaining channel 14 such that the slot 40 of the actuation sled 28 engages the flange 42 of actuation channel 44 to enable re-use of the apparatus.

Although the subject apparatus has been described with respect to preferred embodiments, it will be readily apparent to those having ordinary skill in the art to which it appertains that changes and modifications may be made thereto without departing from the spirit or scope of the subject apparatus as defined by the appended claims.

What is claimed is:

1. A disposable loading unit for use with a surgical stapler, the disposable loading unit comprising:
   a cartridge having a tissue contacting surface and having a plurality of surgical fasteners supported therein;
   an actuator configured to translate through the cartridge to sequentially eject the surgical fasteners, the actuator including a plurality of upstanding cam wedges, the plurality of upstanding cam wedges being monolithically formed from a unitary sheet of material.

2. A disposable loading unit according to claim 1, wherein the plurality of upstanding cam wedges includes two cam wedges and actuator further includes an upstanding flange positioned between the two cam wedges, the upstanding flange and the two upstanding cam wedges being monolithically formed from a unitary sheet of material.

3. A disposable loading unit according to claim 2, further including a knife blade supported on the upstanding flange.

4. A disposable loading unit according to claim 1, further including a plurality of spaced apart projections extending from the tissue contacting surface of the cartridge, the projections being configured to be received within apertures formed in an anvil of a surgical stapler to maintain alignment between the cartridge and anvil during firing of the surgical fasteners.

5. A disposable loading unit according to claim 4, wherein the projections are spaced from the plurality of fasteners.

6. A disposable loading unit according to claim 4, wherein the plurality of spaced apart projections includes two projections.

7. A disposable loading unit according to claim 4, wherein the plurality of upstanding cam wedges includes two cam wedges and the actuator further includes an upstanding flange positioned between the two cam wedges, the upstanding flange and the two upstanding cam being monolithically formed from a unitary sheet of material.

8. A disposable loading unit according to claim 7, further including a knife blade supported on the upstanding flange.

9. A disposable loading unit according to claim 1, further including a knife blade supported on the actuator.

10. A disposable loading unit according to claim 9, wherein the cartridge defines an elongated knife slot which extends through the tissue contacting surface.

11. A disposable loading unit according to claim 10, further including a plurality of spaced apart projections extending from the tissue contacting surface of the cartridge.

12. A disposable loading unit according to claim 11, wherein the plurality of spaced apart projections includes a first projection positioned on one side of the elongated knife slot and a second projection positioned on an opposite side of the elongated knife slot.

13. A disposable loading unit according to claim 9, further including a protective housing positioned to shield the knife blade.

14. A disposable loading unit according to claim 13, wherein the protective housing is formed adjacent a proximal end of the disposable loading unit.

15. A disposable loading unit according to claim 1, wherein the cartridge is formed from a liquid crystal polymer.

16. A disposable loading unit for use with a surgical stapler, the disposable loading unit comprising:
- a cartridge having a tissue contact surface and defining a plurality of surgical fastener slots;
- a plurality of surgical fasteners positioned within the surgical fastener slots;
- an actuator configured to translate through the cartridge to sequentially eject the surgical fasteners from the cartridge; and
- a pair of spaced apart projections extending from the tissue contacting surface of the cartridge, the projections being configured to be received within a pair of apertures formed on an anvil of a surgical stapler to maintain alignment between cartridge and anvil during firing of the staples.

17. A disposable loading unit according to claim 16, further including a plurality of ejectors positioned adjacent the surgical fasteners.

18. A disposable loading unit according to claim 16, wherein the actuator includes two upstanding cam wedges which are monolithically formed from a unitary sheet of material.

19. A disposable loading unit according to claim 18, wherein the actuator further includes an upstanding flange, and the upstanding cam and the two upstanding cam wedges being monolithically formed from a unitary sheet of material.

20. A disposable loading unit according to claim 14, further including a knife blade supported on the upstanding flange.

* * * * *